United States Patent [19]

Powers et al.

[11] Patent Number: 5,086,179
[45] Date of Patent: Feb. 4, 1992

[54] PROCESS FOR THE PREPARATION OF OPTICALLY PURE AMIDES

[75] Inventors: Matthew R. Powers, Barto, Pa.; Raymond D. Youssefyeh, Princeton Junction, N.J.; William L. Studt, Harleysville; Frederick A. Golec, Merion, both of Pa.

[73] Assignee: Rhone-Poulenc Rorer Pharmaceuticals Inc., Ft. Washington, Pa.

[21] Appl. No.: 586,669

[22] Filed: Sep. 24, 1990

Related U.S. Application Data

[60] Continuation-in-part of Ser. No. 351,625, May 15, 1989, Pat. No. 4,959,485, which is a division of Ser. No. 186,824, Apr. 27, 1988, Pat. No. 4,863,921.

[51] Int. Cl.$^5$ .................. C07D 453/02; C07B 53/00; C07C 231/08
[52] U.S. Cl. .................. 546/133; 544/105; 546/79; 546/80; 546/81; 546/83; 546/89; 546/90; 546/101; 546/110; 546/111; 546/93; 546/103; 546/104; 546/107; 546/195; 546/196; 546/197; 546/202; 564/123; 564/172; 564/192
[58] Field of Search .................. 544/105; 546/112, 79, 546/80, 81, 83, 89, 90, 101, 110, 111, 93, 103, 104, 107, 133, 195, 196, 197, 202; 564/123, 172, 192

[56] References Cited

U.S. PATENT DOCUMENTS 4,863,921 9/1987 Youssefyeh et al. ............. 546/112

OTHER PUBLICATIONS

Sidgwich, The Organic Chemistry of Nitrogen, Oxford Univ. Press, London (1945) pp. 144–145.
McOmie, Protective Groups in Organic Chemistry, Plenum Press, London N. York (1973) p. 408.
Zabicky, The Chemistry of Amides, Interscience, New York, N.Y., pp. 830, 831 & 855 (1970).
Cohen et al., J. Am. Chem. Soc., vol. 86, pp. 5611–5616 (1964).
Lacey, J. Chem. Soc., pp. 1633–1639 (1960).

*Primary Examiner*—Bernard Dentz
*Attorney, Agent, or Firm*—Martin F. Savitzky; James A. Nicholson

[57] ABSTRACT

This invention is directed to certain dibenzofurancarboxamides and dibenzofurancarboxamide acids and their use as 5HT$_3$ antagonists having unique CNS, anti-emetic and gastric prokinetic activity void of any significant D$_2$ receptor binding properties. Further, this invention relates to a process for the synthesis of stereoisomeric compounds having such CNS, anti-emetic and gastric prokinetic activity.

19 Claims, No Drawings

PROCESS FOR THE PREPARATION OF OPTICALLY PURE AMIDES

This application is a continuation-in-part of application Ser. No. 351,625, filed on May 15, 1989, now U.S. Pat. No. 4,959,485 which, in turn, is a divisional of application Ser. No. 186,824, filed on Apr. 27, 1988, now issued as U.S. Pat. No. 4,863,921.

BACKGROUND OF THE INVENTION

1. Field of the Invention

This invention relates to dibenzofurancarboxamidetype compounds which exhibit 5HT$_3$-antagonist properties including unique CNS, anti-emetic and gastric prokinetic activity and which are void of any significant D$_2$ receptor binding affinity. This invention relates also to stereospecific processes for the preparation, separation and purification of said compounds.

5-Hydroxytryptamine, abbreviated "5-HT", is commonly known as serotonin. Serotonin is found throughout the body including the gastrointestinal tract, platelets, spleen and brain, appears to be involved in a great number of physiological processes such as neurotransmission at certain neurones in the brain, and is implicated in a number of central nervous system (CNS) disorders. Additionally, serotonin appears to act as a local hormone in the periphery; it is released in the gastrointestinal tract, where it increases small intestinal motility, inhibits stomach and colon motility, and stimulates stomach acid production. Serotonin is most likely involved in normal intestinal peristalsis.

The various physiological activities exerted by serotonin are related to the variety of different receptors found on the surface membrane of cells in different body tissue. The first classification of serotonin receptors included two pharmacologically distinct receptors discovered in the guinea pig ileum. The "D" receptor mediates smooth muscle contraction and the "M" receptor involves the depolarization of cholinergic nerves and release of acetylcholine. Three different groups of serotonin receptors have been identified and the following assignment of receptors has been proposed: D-receptors are 5-HT$_2$-receptors; M-receptors are termed 5-HT$_3$-receptors; and all other receptors, which are clearly not 5-HT$_2$ or 5-HT$_3$, have been referred to as 5-HT$_1$-like and work is being continued on this classification.

5-HT$_3$-receptors have been located in non-neurological tissue, brain tissue, and a number of peripheral tissues related to different responses. It has been reported that 5-HT$_3$-receptors are located on peripheral neurones where they are related to serotonin's (excitatory) depolarizing action. The following subtypes of 5-HT$_3$-receptor activity have been reported: action involving postganglionic sympathetic and parasympathetic neurones, leading to depolarization and release of noradrenaline and acetylcholine, respectively (5-HT$_{3B}$ subtype); action on enteric neurones, where serotonin may modulate the level of acetylcholine (5-HT$_{3C}$ subtype); and action on sensory nerves such as those involved in the stimulation of heart nerve endings to produce a reflex bradycardia (5-HT$_{3A}$ subtype), and also in the perception of pain.

Highly selective 5-HT$_3$-antagonists have been shown to be very effective at controlling and preventing emesis (vomiting) induced by chemotherapy and radiotherapy in cancer patients. The anti-emetic effects of 5-HT$_3$-antagonists in animals exposed to cancer chemotherapy or radiation are similar to those seen following abdominal vagotomy. The antagonist compounds are believed to act by blocking 5-HT$_3$-receptors situated on the cell membranes of the tissue forming the vagal afferent input to the emetic coordinating areas on the brain stem.

Serotonin is also believed to be involved in the disorder known as migraine headache. Serotonin released locally within the blood vessels of the head is believed to interact with elements of the perivascular neural plexus of which the afferent, substance P-containing fibers of the trigeminal system are believed relevant to the condition. By activating specific sites on sensory neuronal terminals, serotonin is believed to generate pain directly and also indirectly by enhancing the nociceptive effects of other inflammatory mediators, for example bradykinin. A further consequence of stimulating the afferent neurones would be the local release of substance P and possibly other sensory mediators, either directly or through an axon reflex mechanism, thus providing a further contribution to the vascular changes and pain of migraine. Serotonin is known to cause pain when applied to the exposed blister base or after an intradermal injection; and it also greatly enhances the pain response to bradykinin. In both cases, the pain message is believed to involve specific 5-HT$_3$-receptors on the primary afferent neurones.

5-HT$_3$-antagonists are also reported to exert potential antipsychotic effects, and are believed to be involved in anxiety. Although not understood well, the effect is believed to be related to the indirect blocking of serotonin 5-HT$_3$-mediated modulation of dopamine activity.

Many workers are investigating various compounds having 5-HT$_3$-antagonist activity.

The development of 5-HT$_3$ agents originated from work carried out with metoclopramide (Beecham's Maxolon, A.H. Robins' Reglan), which is marketed for use in the treatment of nausea and vomiting at high doses. Metoclopramide is a dopamine antagonist with weak 5-HT$_3$-antagonist activity, which becomes more prominent at higher doses. It is reported that the 5-HT$_3$ activity and not the dopamine antagonism is primarily responsible for its anti-emetic properties. Other workers are investigating this compound in connection with the pain and vomiting accompanying migraine.

Merrell Dow's compound MDL-72222 is reported to be effective as an acute therapy for migraine, but toxicity problems have reportedly ended work on this compound. Currently four compounds, A.H. Robins' Zacopride, Beecham's BRL-43694, Glaxo's GR-38032F and Sandoz' ICS-205-930 are in clinical trials for use in chemotherapyinduced nausea and vomiting. GR-38032F is also in clinical trials in anxiety and schizophrenia, and reportedly, Zacopride in anxiety, while ICS-205-930 has been shown to be useful in treating carcinoid syndrome.

Compounds reported as gastroprokinetic agents include Beecham's BRL-24924, which is a serotoninactive agent for use in gut motility disorders such as gastric paresis, audition reflux esophagitis, and is known to have also 5-HT$_3$-antagonist activity.

Metoclopramide, Zacopride, Cisapride and BRL-24924 are characterized by a carboxamide moiety situated para to the amino group of 2-chloro-4-methoxy aniline. BRL-43694, ICS-205-930, GR-38032F and GR-65630 are characterized by a carbonyl group in the 3-position of indole or N-methyl indole. MDL-72222 is a bridged azabicyclic 3,5-dichlorobenzoate, while Zacopride, BRL-24924, BRL-43694 and ICS-205,930 have also bridged azabicyclic groups in the form of a carboxamide or carboxylic ester.

Bicyclic oxygen containing carboxamide compounds wherein the carboxamide is ortho to the cyclic oxygen moiety are reported to have antiemetic and antipsychotic properties in EPO Publ. No. 0234872.

Dibenzofurancarboxamides and 2-carboxamide-substituted benzoxepines are reported to have 5-HT$_3$-antagonist and gastroprokinetic activity in U.S. Pat. Nos. 4,859,683, 4,857,517, 4,924,010 and 4,863,921, all of which are assigned to the same assignee as the present application.

Among the reported compounds are stereoisomers which are synthesized by using chiral synthesis, i.e., asymmetric induction methods of synthesis.

2. Reported Developments

Speaking generally, synthesis with asymmetric induction have been known in the prior art. A synthesis with asymmetric induction is commonly defined as a process in which a chiral unit in an ensemble of substrate molecules induces, by a reaction with achiral units, resulting molecules in such a manner that the stereoisomeric products are produced in unequal amounts. Such an asymmetric syntheses may be of great economic value for excluding or reducing the amount of unwanted isomers when only one of the diastereomers is of use or interest.

The reactants used in an asymmetric synthesis can be at least one chiral component consisting of a chemical reagent, solvent or catalyst. Alternatively, by selection of specific enantiomers as starting compounds, the preferred stereoisomer in a predominant amount can be induced. However, selection of enantiomerically pure intermediates does not always result in a stereoselective synthesis since chirality of an intermediate could be lost due to racemization under one or more sets of reaction conditions. Consequently, synthetic processes typically involve extra reaction steps to accomplish the stereoselective result as well as involve a tedious recrystallization step.

In co-pending application Ser. No. 351,625, the synthesis of the dibenzofurancarboxamides proceeds via condensation of a substituted dibenzofuran-4-carboxylic acid or a 6,7,8,9-tetrahydrodibenzofuran-carboxylic acid or a 5a,6,7,8,9,9a-hexahydrodibenzofuran-4-carboxylic acid or their acid halides or esters with an amine of the formula H$_2$N-R which results in the corresponding carboxamide. The process terminates with a recrystallization step in a relatively poor overall yield. This synthesis is made difficult by the presence of an acid sensitive chiral center which racemizes under mild acid conditions. The present invention is based on a discovery that acid sensitive intermediates can be used in a stereoselective synthesis using conditions which do not affect the product's chiral centers. Using the present invention, yields which are an order of magnitude greater than previously achieved are obtainable with about 95% to about 99% chiral purity.

SUMMARY OF THE INVENTION

This invention relates to a process for the preparation of a substantially optically pure compound containing at least one acid sensitive chiral center and an N-chiral substituted amide comprising removing an N-chiral group from a substantially optically pure N-chiral, N-chiral substituted amide intermediate compound under acid conditions which do not isomerize said acid sensitive chiral center.

A preferred aspect of the invention is the preparation of a substantially optically pure compound of Formula I

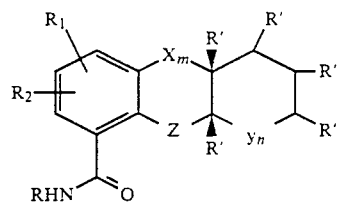

comprising removing the R" group under acidic conditions from the substantially optically pure compound of Formula II

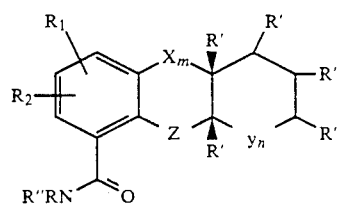

wherein
▶identifies a bond connected to a chiral center;
X and Y are each independently CR'H, O or NR'H;
Z is O, CH$_2$ or S;
m and n are independently 0, 1 or 2;
R' is independently hydrogen, alkyl, halo, alkoxy, aryl, aralkyl or haloalkyl; and vicinal R' groups may together form double bonds;
R$_1$ and R$_2$ are independently hydrogen, alkyl, halo, alkoxy, aryl, aralkyl, haloalkyl, amino, alkylamino, sulfonyl, alkylsulfamyl, or alkylsulfonyl;
R is

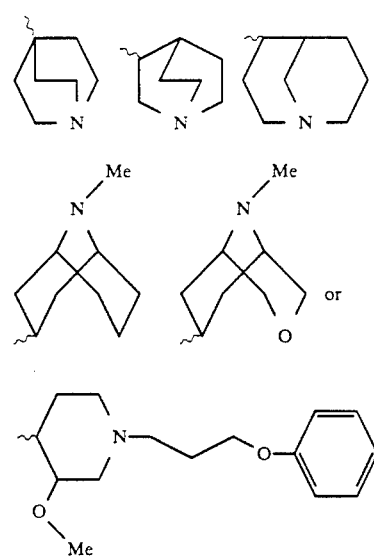

R" is a group capable of removal under acidic conditions including the groups

A is substituted or unsubstituted aryl, heteroaryl or heterocyclic group; and

B is hydrogen, alkyl, carbonyl, hydroxy or alkoxy.

DETAILED DESCRIPTION OF THE INVENTION

As employed above and throughout the disclosure, the following terms, unless otherwise indicated, shall be understood to have the following meanings:

"Alkyl" means, either alone or within the various substitutents, defined hereinbefore, a hydrocarbon having one to about 20 carbon atoms. "Lower alkyl" means alkyl having one to about six carbon atoms, for example, methyl, ethyl, propyl, isopropyl, butyl, isobutyl, amyl and hexyl. Preferred lower alkyl includes methyl, ethyl and propyl.

"Halo" means Cl, Br, I and F.

"Aryl" means a mononuclear and polynuclear aromatic hydrocarbon radical which can be substituted or unsubstituted in one or more positions. Examples of aryl groups include phenyl, naphthyl, anthranyl, phenanthranyl, azulyl and the like which can be substituted with one or more of the substituents. Aryl is preferrably substituted or unsubstituted phenyl or naphthyl. Aryl substituents include hydrogen, alkyl, alkoxy, amino, halo, aryl, aryloxy, carboalkoxy, nitro, dialkylamino, trifluoromethyl, thioalkyl and carbamoyl.

"Aralkyl" means an alkyl group substituted by an aryl radical. The preferred aralkyl groups are lower alkyl groups substituted by phenyl or substituted phenyl. The most preferred aralkyl group is benzyl.

"Heterocyclics" denote mononuclear and polynuclear aromatic hydrocarbon groups in which one or more ring carbons have been replaced by a heteroatom such as nitrogen, oxygen, sulfur, phosphorus or a metal. The preferred heterocyclics are the mononuclear aromatic hydrocarbon groups in which one or more of the carbons have been replaced by oxygen or nitrogen. Preferred heterocyclics include oxacyclobutyl, azacyclobutyl, thiacyclobutyl, oxacyclopentyl, azacyclopentyl, thiacyclopentyl, oxacyclohexyl, azacyclohexyl, thiacyclohexyl, pyridyl, furyl, pyrollyl, quinolyl and indolyl. Substitution by hydrogen, alkyl, alkoxy, halo or acyl can be either on one or more of the heteroatoms or on one or more of the carbon atoms. Substitution on one or more carbon atoms is preferred.

The present invention involves the process of manipulating acid sensitive compounds under acid conditions, the most preferred compounds being acid sensitive carboxylic chiral compounds. Exemplary classes of such compounds include the compounds of Formula I and pharmaceutically acceptable salts thereof.

Another aspect of the present invention involves the preparation of compounds of Formula II above, and which involves reacting a chiral secondary amine with the precursor carboxylic acid halide of Formula III below.

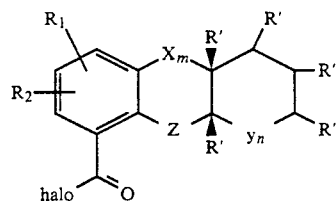

The chiral secondary amine used for reacting with Formula II can be prepared by the following reaction:

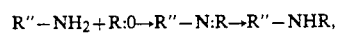

wherein R and R'' denote the previously defined radicals. Examples of compounds of the type of Formula III include acid halides of a substituted dibenzofuran-4-carboxylic acid, 5a,6,7,8,9,9a-hexahydro-benzofuran-4-carboxylic acids and other compounds having carboxylic acid groups.

Preferred compounds are the ones wherein said acid sensitive chiral center comprises an oxy-containing fused ring center.

The present synthesis is applicable not only to the preparation of Formula I but also to its isomers depicted in Formulae IB, IC, ID and IE:

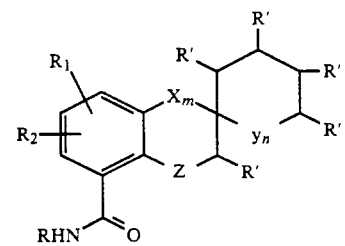

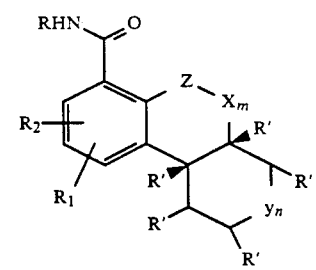

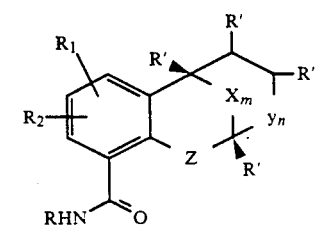

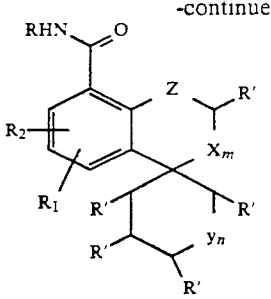
IE

In co-pending application Ser. No. 351,625 which is incorporated herein in its entirety by reference, the process of preparing dibenzofurancarboxamides is as follows:

Condensation of a substituted dibenzofuran-4-carboxylic acid or a 6,7,8,9-tetrahydrodibenzofuran-carboxylic acid or a 5a,6,7,8,9,9a-hexahydrodibenzofuran-4-carboxylic acid or their acid halides or esters with an amine of the formula $H_2N$-R results in the corresponding carboxamide.

In general this reaction may be carried out at decreased temperatures, such as 0° C. by adding ethyl chloroformate to a reaction mixture of the acid in chloroform in the presence of triethylamine. This is then reacted with the amine of the formula $H_2N$-R to obtain the desired product. Condensation may also be carried out in the presence of a dehydrating catalyst such as a carbodiimide in a solvent at normal temperatures. This condensation itself, however, results in relatively low yields of about 4% to 6%.

The present invention utilizes chiral starting materials, i.e., acid or amines in the synthetic process in which condensation of the acid halides of a substituted dibenzofuran-4-carboxylic acid or a 5a,6,7,8,9,9a-hexahydrodibenzofuran-4-carboxylic acid with a secondary amine of the formula HN-RR" results in the corresponding N-protected carboxamide. Treatment of this compound with selective acidic conditions results in the compounds of general Formulae I, IB, IC, ID or IE. In general the acid chloride is formed by reaction of the acid with thionyl chloride in toluene at elevated temperature. After the freebase of the secondary amine has been made, with NaOH, it is coupled with the acid chloride in toluene at elevated temperature. The resulting secondary amide is then treated with acid, for example, HCl in a polar aprotic solvent, to obtain the desired product absent racemization of the fused ring chiral centers.

The acid halide formation is accomplished as follows:

A solution of a carboxylic acid in toluene is heated to about 35° to about 40° C. under nitrogen. To this is added about 1.5 to about 2 equivalents of thionyl chloride dropwise over about 15 min. The reaction is allowed to stir under nitrogen at about 40° C. while being monitored by TLC. When the reaction is complete the nitrogen is turned up and the reaction vessel is set up for stripping off the excess thionyl chloride and solvent under vacuum. The nitrogen is turned down to a minimum and the reaction mixture is heated to about 70° C. at 2-4 mm vaccum. The heat is then shut off and the material is stored- in the reaction flask under nitrogen.

The coupling reaction and deprotection is typically accomplished as follows:

A toluene solution of the acid chloride is placed in an addition funnel under a blanket of nitrogen. A toluene solution of free secondary amine is set up in a flask with a mechanical stirrer. The acid chloride solution is then added dropwise at about 25° C. over approximately 30 minutes. The reaction is held at about 40° C. until addition is completed, then more toluene is added and the reaction is cooled to about 5° C. and filtered. A sticky white solid is obtained which is washed with another 5° C. portion of toluene to yield the product.

Deprotection of the amide of Formulae II, IIB, IIC, IID or IIE is accomplished by heating it with about 1.5 to about 2 equivalents of about 20-40% HCl, preferably about 37% HCl, in an aprotic polar solvent. The reacting temperature is maintained at about 50 to about 60° C.. Exemplary solvents include ketones, alkylsulfoxides, alkylformamides and the like. The most preferred solvents are dialkyl ketones such as acetone.

Certain compounds of this invention have at least more than one asymmetric carbon atoms. As a result, those compounds of Formula I may be obtained either as racemic mixtures, diastereoisomeric mixtures or as individual enantiomers. When two or three asymmetric centers are present the product may exist as mixtures of two or four diastereomers. Of course it is understood that certain other compounds within the scope of this invention could have a number of stereocenters. In general, a compound with x stereocenters can have a maximum of $2^x$ stereoisomers. Therefore, a compound having three such centers gives rise to a maximum of eight stereoisomers, while one having four produces sixteen, etc. The product may be synthesized as a mixture of the isomers and then the desired isomer separated by conventional techniques such as chromatography or fractional crystallization from which each diastereomer may be resolved. On the other hand, synthesis may be carried out by known stereospecific processes using the desired form of the intermediate which would result in obtaining the desired stereospecificity.

The resolution of the compounds of this invention and their starting materials may be carried out by known procedures. Incorporation by reference is hereby made to the four volume compendium *Optical Resolution Procedures for Chemical Compounds:* Optical Resolution Information Center, Manhattan College, Riverdale, N.Y. Such procedures are useful in the practice of this invention. A further useful reference is *Enantiomers, Racemates and Resolutions:* Jean Jacques, Andre Collet and Samuel H. Wilen; John Wiley & Sons, Inc., New York, 1981. Basically, the resolution of the compounds is based on the differences in the physical properties of diastereomers. Conversion of the racemates into a mixture of diastereomers by attachment of an enantiomerically pure moiety results in forms that are separable by fractional crystallization, distillation or chromatography.

Compounds of the present invention of Formula I may be prepared by the following representative examples.

In the examples chiral purity of a material is measured on a chiracel OD HPLC column with a hexane, ethanol, diethylamine (90:10:01) mobile phase at a flow rate of 1 ml per minute and a wavelength of 254 mm.

EXAMPLE 1 a. (R)-α-METHYLBENZYL-(S)-3-AMINOQUINU-CLIDINE DIHYDROCHLORIDE

To a solution of 300 g (2.4 mol) of 3-quinuclidinone in 1100 ml toluene is added 280 g (2.3 mol) of R-(+)-α-methyl-benzylamine, and 2.8 g of p-toluenesulfonic acid. The reaction is heated to reflux with stirring, and the water formed is removed by a Dean Stark trap. Once the theoretical amount of water is removed, 450 ml of toluene is distilled off at atmospheric pressure. The rest of the solvent is removed under reduced pressure. The dark amber oil remaining is filtered to yield 540 g (99.5%) product which is 92A% pure by HPLC.

A solution of 540 g (2.3 mol) of R-α-methylbenzyl-3quinuclidinimine in 1600 ml methanol is cooled in an ice bath to 10° C.. Potassium borohydride (120 g, 2.2 mol), is added to this solution in small portions, with stirring, over 1 hour. The temperature is held between 10°-20° C. during the addition. Once the addition is complete, the reaction is allowed to come to room temperature. HPLC is used to monitor the reaction. Upon completion the reaction is filtered, and the methanol removed by evaporation under reduced pressure. The solid potassium salts formed are removed by vacuum filtration, and triturated with acetone (2×500 ml). The acetone washes are combined with the oil and the mixture is reduced to one-half its volume under vacuum. More potassium salts formed which are removed by filtration through a bed of celite. The rest of the solvent is then removed under vacuum and the dark amber oil left is filtered through another bed of celite. A yield of 508.9 g (92%) of clear amber oil is obtained. The oil is dissolved in 200 ml of 2-propanol and a solution of 559 g of concentrated HCl in 500 ml of 2-propanol is added in small portions. The temperature is held between 25°-50° C. by an ice bath. After the addition is complete, continued cooling to 10° C., leads to crystallization. An additional 700 ml of 2-propanol is added to keep the slurry mixable. This material is placed in the refrigerator for 12 hours then filtered. The filter cake is washed with 500 ml of cold 2-propanol. A yield of 310 g of 98A% chiral pure material is obtained as a white solid. Another 20 g of 97A% pure material is obtained by adding 400 ml of acetone to the above 2-propanol wash and cooling it. All the mother liquors are combined and 1 l of solvent removed under reduced pressure. Upon cooling 200 ml of 1:1 acetone:2-propanol is added to keep the mixture mixable. A yield of 118 g of 92A% chiral purity is obtained after filtration. The mother liquors are again reduced by two thirds under vacuum. Another 100 ml of 1:1 acetone:2-propanol is added to keep the material mixable. Cooling in the refrigerator for 48 hours, then filtering, yields 200 g of material which is only 14A% of the desired diastereomer. Crops 2 (20 g, 97A%) and 3 (118 g, 92A%) are combined and recrystallized from 475 ml ethanol to yield 110 g of 100A% chiral purity material. A total of 420 g of material of >98A% chiral purity is obtained.

b. 4-[N-(1-AZABICYCLO[2.2.2]OCTANE-3(S)-YL)]-2-CHLORO-[5a(S1-9a(S1)-5a,6,7,8,9,9a-HEXAHYDRO)]DIBENZOFURANCARBOXA-MIDE-HYDROCHLORIDE

A solution of 3 g (0.0118 mol) of 2-chloro-[5a(S)-9a(S)-(5a,6,7,8,9,9a-hexahydro)]dibenzofuran-4-car-boxylic acid in 15 ml of toluene, was heated to 35°-40° C. under nitrogen. To this was added 1.7 g (0.0141 mol) of thionyl chloride, dropwise over 15 minutes. The reaction is allowed to stir under nitrogen at 40° C. while being monitored by TLC. When the reaction is complete, the nitrogen is turned up and the reaction vessel is set up for stripping off the excess thionyl chloride and solvent under vacuum. The nitrogen is turned down to a minimum and the reaction mixture is heated to 70° C. at 2-4 mm vacuum. The heat is then shut off and the material is stored in the reaction flask under nitrogen.

To a solution of 4.5 g (0.15 mol) of (R)-α-methylben-zyl-(S)-3-aminoquinuclidine dihydrochloride in 10 ml of water and 5 ml of methanol was added 2.4 g (0.03 mol) of 50% NaOH. This solution was stirred for five minutes and then extracted with toluene (2×20 ml). The toluene extracts were combined, washed with 40 ml of water and dried with magnesium sulfate. The solvent was then removed under vacuum to yield 3.1 g (0.13 mol) (90%) of (R)-α-methylbenzyl-(S)-3-aminoquinu-clidine as the free base. This oil is dissolved in 10 ml of toluene, and used as is in the subsequent coupling reaction.

While the solvent is being stripped off above, 20 ml of toluene is added to the acid chloride from step 1. This solution is placed in an addition funnel under a blanket of nitrogen. When the final toluene solution of free amine is obtained from step 2, it is set up in a flask with a mechanical stirrer. The acid chloride from step 1 is added dropwise at 25° C. over approximately 30 minutes. The reaction is held at 40° C. until it has stopped by HPLC. Once the reaction has stopped, 10 ml of toluene is added and the reaction is cooled to 5° C. and filtered. A sticky white solid is obtained which is washed with another 10 ml of 5° C. toluene to yield 4 g (67%) of product which is 95% pure by chiral HPLC.

A 1 g (.002 mol) sample of the benzyl protected amide is refluxed in 20 ml of acetone with 0.4 ml (.004 mol) of concentrated HCl (37%) added. The reaction is refluxed and followed by HPLC. After 4 hours there is 55% 4-[N-(1-azabicyclo[2.2.2]octane-3(S)-yl)]-2-chloro-[5a(S)-9a(S)-(5a,6,7,8,-9,9a-hexahydro)]dibenzofurancarboxamide hydrochloride present by HPLC and further refluxing does not increase this percentage. The reaction mixture is cooled and then evaporated to a sticky solid under vacuum. This material forms a white solid when 5 ml of acetone is added to it. This slurry is cooled to 5° C. and filtered to yield 600 mg (76%) of 95% pure 4-[N-(1-azabicyclo[2.2.2]octane-3(S)-yl)]-2-chloro-[5a(S)-9a(S)-(5a,6,7,8,9,9a-hexahy-dro)]dibenzofurancarboxamide hydrochloride.

EXAMPLE 2

The various compounds of Formulae I made by the method of this invention can be prepared as above using the desired starting materials. The following is representative of the compounds prepared by the method of this invention:

4-[N-(1-azabicyclo[2.2.2]octane-3(R)-yl)]-2-chloro-[5a(S)-9a(S)-(5a,6,7,8,9,9a-hexahydro)]dibenzofurancar-boxamide hydrochloride. Yield: 80%. Chiral purity: 99%.

4-[N-(1-azabicyclo[2.2.2]octane-3(R)-yl)]-2-chloro-[5a(R)-9a(R)-(5a,6,7,8,9,9a-hexahydro)]dibenzofuran-carboxamide hydrochloride. Yield: 70%. Chiral purity: 95%.

4-[N-(1-azabicyclo[2.2.2]octane-3(S)-yl)]-2-chloro-[5a(R)-9a(R)-(5a,6,7,8,9,9a-hexahydro)]dibenzofuran-carboxamide hydrochloride. Yield: 78%. Chiral purity: 96%.

The compounds of this invention may be readily converted to their non-toxic acid addition salts by customary methods in the art. The non-toxic salts of this invention are those salts the acid component of which is pharmacologically acceptable in the intended dosages, including those prepared from inorganic acids such as hydrochloric acid, hydrobromic acid, sulfuric acid, nitric acid and phosphoric acid, and from organic acids such as methane sulfonic acid, benzenesulfonic acid, acetic acid, propionic acid, maleic acid, succinic acid, glycolic acid, lactic acid, salicylic acid, benzoic acid, nicotinic acid, phthalic acid, stearic acid, oleic acid, etc.

Compounds within the scope of this invention exhibit useful gastric prokinetic and anti-emetic properties and lack $D_2$ receptor binding activity. As such they possess therapeutic value in the treatment of upper bowel motility and gastro-esophageal reflux disorders. Further, the compounds of this invention may be useful in the treatment of disorders related to impaired gastrointestinal motility such as retarded gastric emptying, dyspepsia, flatulence, esophageal reflux, peptic ulcer and emesis. Compounds within the scope of this invention exhibit 5-HT$_3$ antagonism and are considered to be useful in the treatment of psychotic disorders such as schizophrenia and anxiety and in the prophylaxis treatment of migraine and cluster headaches. Compounds of this invention are selective in that they have little or no dopaminergic antagonist activity.

Various tests in animals can be carried out to show the ability of the compounds of this invention to exhibit pharmacological responses that can be correlated with activity in humans. These tests involve such factors as the effect of the compounds of Formula I on gastric motility, emesis, selective antagonism of 5-HT$_3$ receptors and their $D_2$ dopamine receptor binding properties.

It has been found that the compounds of this invention when tested in the above variety of situations show a marked activity.

One such test is the "Rat Gastric Emptying: Amberlite Bead Method". This test is carried out as follows:

The study is designed to assess the effects of a test agent on gastric emptying of a solid meal in the rat. The procedure is a modification of those used in L. E. Borella and W. Lippmann (1980) *Digestion* 20: 26-49.

Procedure

Amberlite ® beads are placed in a phenol red solution and allowed to soak for several hours. Phenol red serves as an indicator, changing the beads from yellow to purple as their environment becomes more basic. After soaking, the beads are rinsed with 0.1 NaOH to make them purple and then washed with deionized water to wash away the NaOH.

The beads are filtered several times through 1.18 and 1.4 mm sieves to obtain beads with diameters in between these sizes. This is done using large quantities of deionized water. The beads are stored in saline until ready to use.

Male Sprague-Dawley rats are fasted 24 hours prior to the study with water ad libitum. Rats are randomly divided in treatment groups with an N of 6 or 7.

Test agents are prepared in 0.5% methylcellulose and administered to the rats orally in a 10 ml/kg dose volume. Control rats receive 0.5% methylcellulose, 10 ml/kg p.o. One hour after dosing, rats are given 60 Amberlite ® beads intragastrically. The beads are delivered via a 3 inch piece of PE205 tubing attached to a 16 gauge tubing adapter and syringe. A small piece of PE 50 tubing is placed inside the tubing adapter to prevent the beads from being pulled back into the syringe. The beads are flushed into each rat's stomach with 1 ml saline.

Rats are sacrificed 30 minutes after receiving the beads and their stomachs are removed. The number of beads remaining in each stomach is counted after rinsing the beads with NaOH.

The number of beads remaining in each stomach is subtracted from 60 to obtain the number of beads emptied. The mean number of beads $\pm$S.E.M. is determined for each treatment group. The percent change from control is calculated as follows:

$$\frac{\text{Mean Control Group} - \text{Mean Test Agent Group}}{\text{Mean Control Group}} \times 100$$

Statistical significance may be determined using a t-test for independent samples with a probability of 0.05 or less considered to be significant.

In order to demonstrate the ability of the compounds of this invention as anti-emetic agents, the following test for "Cisplatin-Induced Emesis in the Ferret" may be used. This test is a modified version of a paper reported by A. P. Florezyk, J. E. Schurig and W. T. Brodner in *Cancer Treatment Reports:* Vol. 66, No. 1, January 1982.

Cisplatin had been shown to cause emesis in the dog and cat. Florczyk, et al. have used the ferret to demonstrate the same effects.

Procedure

Male castrated, Fitch ferrets, weighing between 1.0 and 1.5 kg have an indwelling catheter placed in the jugular vein. After a 2-3 day recovery period, the experimental procedure is begun.

30 minutes prior to administration of cisplatin, ferrets are dosed with the compound in 0.9% saline (i.v.) at a dose volume of 2.0 ml/kg.

45 minutes after administration of cisplatin, ferrets are again dosed with the 0.9% saline (i.v.) mixture at a dose volume of 2.0 ml/kg.

Cisplatin is administered (i.v.) 30 minutes after the first dosing with 0.9% saline. Cisplatin, 10 mg/kg is administered in a dose volume of 2.0 ml/kg.

The time of cisplatin administration is taken as time zero. Ferrets are observed for the duration of the experiment (4 hours). The elapsed time to the first emetic episode is noted and recorded, as are the total number of periods of emesis.

An emetic (vomiting) episode is characterized by agitated behavior, such as pacing around the cage and rapid to and from movements. Concurrent with this behavior are several retching movements in a row, followed by a single, large, retch which may or may not expulse gastric contents. Immediately following the single large retch, the ferret relaxes. Single coughs or retches are not counted as vomiting episodes.

D-2 Dooamine Receptor Binding Assay

The D-2 dopamine receptor binding assay has been developed with slight modifications using the method of Ian Cresse, Robert Schneider and Solomon H. Snyder, *Europ. J. Pharmacol.* 46: 377-183 (1977). Spiroperidol is a butyrophenone neuroleptio whose affinity for dopamine receptors in brain tissue is greater than that of any other known drug. It is a highly specific D-1 dopamine (non-cyclase linked) receptor agent with $K_1$ values of 0.1-0.5 for D-2 inhibition and 300 nM for D-1 inhibition.

Sodium ions are important regulators of dopamine receptors. The affinity of the D-2 receptor is markedly enhanced by the presence of millimolar concentrations of sodium chloride. The Kd in the absence and presence of 120 mM sodium chloride is 1.2 and 0.086 nM respectively. Sodium chloride (120 mM) is included in all assays as a standard condition.

The caudate nucleus (corpus striatum) is used as the receptor source because it contains the highest density of dopamine receptors in the brain and periphery.

Procedure

Male Charles-River rats weighing 250-300g are decapitated and their brain removed, cooled on ice, and caudate dissected immediately and frozen on dry ice. Tissue can be stored indefinitely at $-70°$ C. For assay caudate is homogenized in 30 ml of tris buffer (pH 7.7 at 25° C.) using the polytron homogenizer. The homogenate is centrifuged at 40,000 g (18,000-19,000 RPM in SS-34 rotor) for 15 minutes. Pellet is resuspended in fresh buffer and centrifuged again. The final pellet is resuspended in 150 volumes of assay buffer.

Specific $^3$H-spiroperidol binding is assayed in a total 2 ml reaction volume consisting of 500 $\mu$l of caudate homogenate, 50 mM tris buffer (pH 7.4 at 35° C.), 5 mM $MgSO_4$, 2 mM EDTA.2NA, 120 mM NaCl, 0.1% ascorbic acid, 0.4 nM $^3$H-spiroperidol and test compound or assay buffer. When catecholamines are included in the assay, 10 $\mu$M pargyline should be included in the reaction mixture to inhibit monoamine oxidase. Samples are incubated at 37° C. for 30 minutes followed by addition of 5 ml ice cold 50 mM TRIS (pH 7.7 at 25° C.) and filtration through GF/B glass fiber filters on a Brandel Receptor Binding Filtration apparatus. Filters are washed twice with an additional 5 ml of tris buffer each. Assay groups are performed in triplicate and 1 $\mu$M d(+) butaclamol is used to determine nonspecific binding. Filters are placed in vials containing 10 ml of Ecoscint phosphor, shaken for 30 minutes and dpm determined by liquid scintillation spectrophotometry using a quench curve. Proteins are determined by the method of Bradford, M. Anal. Biochem 72, 248 (1976) using Bio-Rad's coomassie blue G-250 dye reagent. Bovine gamma globulin supplied by Bio-Rad is used as the protein standard.

Bezold-Jarisch Effect in Anaesthetized Rats

Male rats 260-290 g are anaesthetized with urethane 1.25 g/kg$^{-1}$ i.p., and trachea cannulated. The jugular vein is cannulated for intravenous (i.v.) injection of drugs. Blood pressure is recorded from a cannula in the left carotid artery and connected to a heparin/saline-filled pressure transducer. Continuous heart rate measurements are taken from the blood pressure recordings. The Bezold-Jarisch effect is evoked by rapid, bolus i.v. injections of 5-HT and measurements are made of the fall in heart rate. In each rate, consistent responses are first established with the minimum dose of 5-HT that evokes a clear fall in heart rate. Injections of 5-HT are given every 12 minutes and a dose-response curve for the test compound is established by injecting increasing doses of compound 5 minutes before each injection of 5-HT. The effect of the compound on the 5-HT-evoked bradycardia is calculated as a percent of the bradycardia evoked by 5-HT before injection of compound.

In separate experiments to measure the duration of 5-HT antagonism caused by the compounds of this invention, a single dose of compound is injected 5 minutes before 5-HT, and the effects of 7 repeated challenges with 5-HT are then monitored. The effects of the compound on the efferent vagal limb of the Bezold-Jarisch reflex are checked by electrically stimulating the peripheral end of a cut vagus nerve. Unipolar electrical stimulation is applied every 5 minutes via a pair of silver electrodes, using 1 ms rectangular pulses in 5 strains with a maximally-effective voltage (20 V at 10 Hz). Pulse frequency may vary from 5-30 $H_2$ and frequency-response curves are constructed before and 10 minutes after i.v. injection of a single dose of compound.

The results of these above tests indicate that compounds within the scope of this invention exhibit a valuable balance between the peripheral and central action of the nervous system and may be useful in the treatment of disorders related to impaired gastro-intestinal motility such as gastric emptying, dyspepsia, flatulence, esophageal reflux and peptic ulcer and in the treatment of disorders of the central nervous system such as psychosis.

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepthelially including transdermal, ophthalmic, sublingual and buccal; topically including ophthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, trochees, capsules, elixirs, suspensions, syrups, wafers and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, trochees, pills, capsules and the like may also contain the following: A binder such as gum tragacanth, acacia, corn starch or gelating; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a freebase or pharmacologically acceptable salt can be prepared in water suitably mixed with a surfactant such as hydroxy-propylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol, and liquid polyethylene glycol, and the like), suitable mixtures thereof, and vegetable oils. The proper fluidity can be maintained, for example, by the use of a costing such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions of agent delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredients from those enumerated above. In the case of sterile powders for the preparation of sterile injectable solutions, the preferred methods of preparation are vacuum drying and the freeze drying technique with yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility ad chemical nature of the compound, chosen route of administration and standard pharmaceutical practice.

The physician will determine the dosage of the present therapeutic agents which will be most suitable for prophylaxis or treatment and will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from 0.1 to 20 mg or from about 0.01 mg to about 50 mg/kg of body weight per day and higher although it may be administered in several different dosage units from once to several times a day. Higher dosages are required for oral administration.

What is claimed is:

1. A process for the preparation of a substantially optically pure secondary amide containing at least one acid sensitive chiral center in the acyl portion of the amide and an N-chiral group, comprising removing an N acid-removable-chiral group from a substantially optically pure N-chiral, N-chiral disubstituted amide compound under acid conditions which do not isomerize said acid sensitive chiral center, wherein said acid removable N-chiral group is capable of forming a stabilized carbonium ion and comprises a chiral alkyl group substituted with aryl or heteroaryl.

2. A process according to claim 1 wherein said acid sensitive chiral center comprises an oxy-containing fused ring carbocycle.

3. A process according to claim 1 wherein said acidic conditions comprise hydrochloric acid in admixture with a polar aprotic solvent for a time and temperature sufficient to remove said N-chiral group.

4. A process according to claim 3, wherein said conditions comprise heating in a mixture of concentrated hydrochloric acid and a ketone.

5. A process according to claim 4 wherein said ketone is acetone.

6. A process according to claim 1 for the preparation of an optically pure secondary amide of the formula

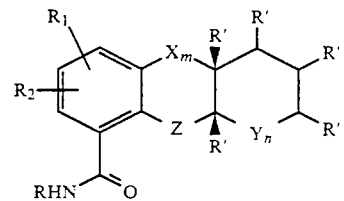

comprising treating a compound of the formula

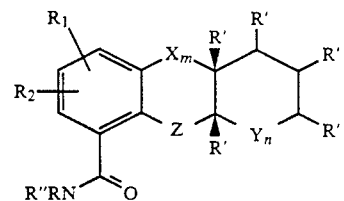

under acidic conditions sufficient to remove selectively the R" group without isomerization of the chiral enters thereof, wherein:

▶ identifies a bond to a chiral center;
X and Y are each independently CH'H,O or NR'H;
Z is O, $CH_x$ or S;
m and n are independently 0, 1 or 2;
R' is independently hydrogen, alkyl, halo, alkoxy, aryl, aralkyl or haloalkyl; and vicinal R' groups may together form double bonds;

R₁ and R₂ are independently hydrogen, alkyl, halo, alkoxy, aryl, aralkyl, haloalkyl, amino, alkylamino, sulfonyl, alkylsulfamyl, or alkylsulfonyl;

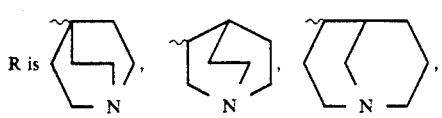

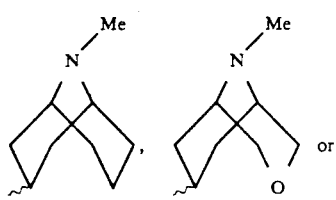

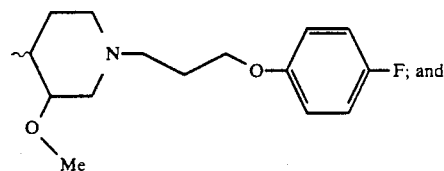

an acid removable chiral group capable of forming a stabilized carbonium ion comprising a chiral alkyl group substituted with aryl or heteroaryl.

7. A process according to claim 1 wherein said N,N-disubstituted amide intermediate is formed by combining (a) a substantially optically pure acid halide of a carboxylic acid compound having at least one acid sensitive chiral center, and (b) an optically pure secondary amine substituted with an N-chiral group and with an N-chiral group capable of removal under acid conditions.

8. A process for the synthesis of a compound of the formula

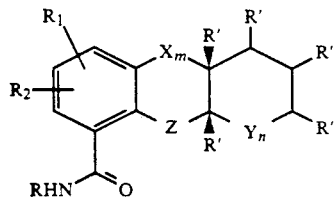

or a pharmaceutically acceptable salt thereof comprising:

reacting a chiral secondary amine NHRR″ wherein both of the substituents are chiral with a compound of the formula

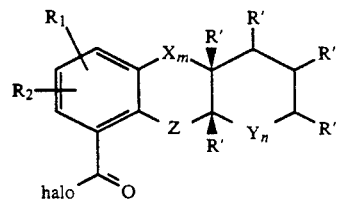

to obtain a compound of the formula

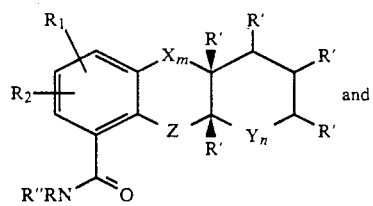

removing the R″ protective group therefrom under said conditions; wherein

▶ identifies a bond to a chiral center;

X and Y are each independently CH′H, O or NR′H;

Z is O, CH₂ or S;

m and n are independently 0,1 or 2;

R′ is independently hydrogen, alkyl, halo, alkoxy, aryl, aralkyl or haloalkyl; and vicinal R′ groups may together form double bonds;

R₁ and R₂ are independently hydrogen, alkyl, halo, alkoxy, aryl, aralkyl, haloalkyl, amino, alkylamino, sulfonyl, alkylsulfamyl, or alkylsulfonyl;

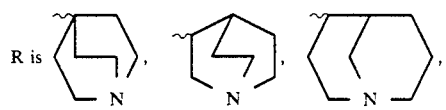

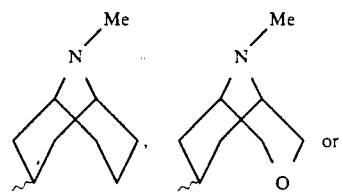

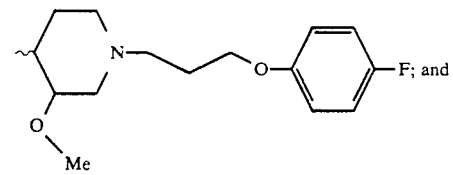

R″ is an acid removable chiral group capable of forming a stabilized carbonium ion comprising a chiral alkyl group substituted with aryl or heteroaryl.

9. The process of claim 8 further comprising forming a salt of the N-protected carboxamide by treatment with an inorganic acid.

10. The process of claim 8 wherein said chiral secondary amine is R-α-methylbenzyl-(S)-3-aminoquinuclidine.

11. The process of claim 10 wherein said R-α-methylbenzyl-(S)-3-aminoquinuclidine is prepared by: condensing R-α-methylbenzylamine with 3-quinuclidinone to form R-α-methylbenzyl-3-quinuclidinimine; and reducing said R-α-methylbenzyl-3-quinuclidinimine with potassium borohydride.

12. The process of claim 11 wherein said condensing is by reflux in toluene.

13. The process of claim 12 wherein said condensing is in the presence of a catalytic amount of paratoluene sulfonic acid.

14. The process of claim 8 wherein said chiral secondary amine is condensed with an acid halide or a substituted dibenzofuran-4-carboxylic acid to form an N-protected carboxamide.

15. The process of claim 8 wherein said chiral secondary amine is condensed with a substituted 5a,6,7,8,9,9a-hexahydro-dibenzofuran-4-carboxylic acid to form an N-protected carboxamide.

16. The process of claim 15 wherein said substituted 5a,6,7,8,9,9a-hexahydrodibenzofuran-4-carboxylic acid is 2-chloro-dibenzofuran-4-carboxylic acid.

17. The process of claim 8 wherein said chiral secondary amine is S-α-methylbenzyl-(R)-3-aminoquinuclidine.

18. The process of claim 17 wherein said S-α-methylbenzyl-(R)-3-aminoquinuclidine is prepared by: condensing S-α-methylbenzylamine with 3-quinuclidinone to form S-α-methylbenzyl-3-quinuclidinimine; and reducing said S-α-methylbenzyl-3-quinuclidinimine with potassium borohydride.

19. A process for the synthesis of 4-[N-(1-azabicyclo[2.2.2]⇌octane-3(S)-yl]-2-chloro-[5a(S)-9a(S)-(5a,6,7,8,9,9a-heaxahydro)]dibenzofurancarboxamide or acid addition salt comprising the steps of: condensing (R)-α-methylbenzyl-(S)-3-aminoquinuclidine with 2-chloro-[5a(S)-9a(S)-(5a,6,7,8,9,9a-hexahydro)]-dibenzofuran-4-carbonylchloride to yield 4-[N-{1-azabicyclo[2.2.2]octane-3(S)-yl}-{N-(R)-α-methylbenzyl}]-2-chloro-[5a(S)-9a(S)-(5a,6,7,8,-9,9a-hexahydro)]-dibenzofurancarboxamide acid salt; and treating said hydrochloride salt under acid conditions.

* * * * *